(12) United States Patent
Keilman et al.

(10) Patent No.: US 8,142,362 B2
(45) Date of Patent: *Mar. 27, 2012

(54) ENHANCED PRESSURE SENSING SYSTEM AND METHOD

(75) Inventors: George W. Keilman, Bothell, WA (US); Timothy Johnson, Bothell, WA (US)

(73) Assignee: Pacesetter, Inc., Sylmar, CA (US)

( * ) Notice: Subject to any disclaimer, the term of this patent is extended or adjusted under 35 U.S.C. 154(b) by 948 days.

This patent is subject to a terminal disclaimer.

(21) Appl. No.: 12/109,290

(22) Filed: Apr. 24, 2008

(65) Prior Publication Data

US 2009/0270740 A1      Oct. 29, 2009

(51) Int. Cl.
*A61B 5/0215* (2006.01)
*G01L 7/08* (2006.01)
(52) U.S. Cl. ............... 600/486; 73/715; 73/716
(58) Field of Classification Search .............. None
See application file for complete search history.

(56) References Cited

U.S. PATENT DOCUMENTS

| 7,278,318 B2 * | 10/2007 | Dannhauer et al. | 73/716 |
| 7,568,394 B1 * | 8/2009 | Keilman et al. | 73/715 |

* cited by examiner

*Primary Examiner* — Cathy Kingdon Worley (57) ABSTRACT

An enhanced pressure sensing system and method use an external diaphragm to address issues involved with accurate and prolonged measurement of fluid pressure, such as of blood flowing in a vascular structure. Some external diaphragms include a metallized layer or other highly impermeable layer to furnish a high degree of seal at least near to hermetic grade. As temperature of the intermediary fluid changes, the external diaphragm is able to move in a direction that minimizes differential pressure across the external diaphragm over an operational temperature range thereby reducing pressure change of the intermediary fluid due to change in temperature of the intermediary fluid. Relatively smooth hydrodynamic surfaces can be used as well as a bi-layer construction.

58 Claims, 9 Drawing Sheets

ENHANCED PRESSURE SENSING SYSTEM AND METHOD

BACKGROUND OF THE INVENTION

1. Field of the Invention

The present invention is directed generally to pressure sensor systems.

2. Description of the Related Art

A miniature pressure sensor system can include a housing with an external diaphragm that directly contacts a sampled fluid, a sensor (enclosed by the housing) that is not in direct contact with the sampled fluid, and an internal intermediary fluid (contained within the housing) that contacts the external diaphragm and also contacts the sensor to allow the sensor to measure pressure of the sampled fluid. In order to accurately transfer pressure from the sampled fluid to the sensor, among other things, the external diaphragm must be as compliant with the sampled fluid as possible. Unfortunately, temperature changes can cause the intermediary fluid to expand or contract at a different rate than pertinent components of the housing thereby inducing pressure changes in the intermediary fluid unrelated to pressure status of the sampled fluid and consequently, affecting accuracy of pressure measurements of the sampled fluid.

Versions of microelectromechanical systems (MEMS) can determine pressure levels of a fluid being measured and can be especially useful for miniature pressure sensor systems due to their small size. MEMS pressure sensor dies typically have a MEMS diaphragm fabricated to be integrated in the MEMS die and are typically positioned to directly contact the fluid being measured. In some applications of miniature pressure sensor systems, a MEMS diaphragm may not be compatible with the particular environment and/or the fluid being measured such as intraluminal fluids found in biological environments like with blood flows in vascular structures.

In other cases the MEMS pressure sensor die may be part of other components sharing a common package. These situations can reduce the desirability of the MEMS diaphragm directly contacting the fluid being measured. In such cases the MEMS diaphragm may be enclosed inside of a housing having an external diaphragm and a internal intermediary fluid therebetween. The external fluid is able to contact the sampled fluid to be measured and the intermediary fluid transfers pressure experienced by the external diaphragm on to the MEMS diaphragm.

Selection of conventional diaphragms used in non-miniature pressure sensor systems for use as an external diaphragm in miniature pressure sensor systems involving MEMS can be problematic. For instance, highly-stable conventional pressure sensor systems for use in industrial applications are typically quite large (>15 mm in diameter), having large-diameter, thin metal corrugated diaphragms. Further, these industrial applications typically involve a wide range of pressures, which allows such large sized industrial diaphragms to impart a very small error in pressure measurement relative to the range of pressures being measured.

In applications involving miniature pressure sensor systems, such as with vascular structures, where the size of a pressure sensor system is relatively small and where measured pressures have small ranges and/or values, use of conventional diaphragms for an external diaphragm raise scaling issues when going from the larger scale applications to the smaller scale applications. For instance, in some smaller scale applications, such as biomedical applications in general and involving pulmonary artery pressure measurement in particular, a normal pressure range may be only from 0 Torr to 20 Torr on a gage basis.

In some of these cases (such as in an implanted medical device), an atmospheric reference pressure is not available, which requires pressure measurement using an absolute pressure range from 760 to 780 Torr absolute that leaves little room for error on a percentage basis and causes a high demand for accuracy and stability over both time and temperature. For example, typically, medical diagnosis under such conditions requires a measurement to within 1 Torr, or 0.13% on an absolute scale.

Some conventional miniature pressure sensor systems are filled with silicone or fluorosilicone gel coatings and use no diaphragm. The operational life spans of the coatings tend to be short due to the coatings so are not appropriate where sensor elements require long-term protection from corrosive body fluids. In addition, these conventional coatings expose sample intravascular blood to surfaces that are not fully hemocompatible, such as found with the silicone or fluorosilicone gel materials used for the coatings, which can lead to thrombus (clot) formation within a vascular structure hosting such a miniature pressure sensor system.

In addition, external diaphragm surface geometry is of importance in such cases when a miniature sensor system is to be placed in flowing fluids such as flowing blood. An undesirable geometry for fluid flow applications includes rough, non-hydrodynamic surfaces that can induce shearing motion within a blood flow thereby introducing a potential activation mechanism of a coagulation cascade, leading to thrombus (clot) formation.

DETAILED DESCRIPTION OF THE INVENTION

An enhanced pressure sensing system and method of miniature size, such as for implantation in a biological structure such as a lumen, vessel, or other tubular structure, is discussed herein that addresses issues involved with accurate and prolonged measurement of fluid pressure, such as of blood flowing in a vascular structure. The issues include providing at least close to hermetic isolation between a sampled fluid and a pressure sensor, providing high compliance levels of the miniature pressure sensor system with the host environment (such as a vascular structure containing flowing blood), and maintaining accurate correspondence between internal intermediary fluid pressure and sampled fluid pressure, so that sampled fluid pressure state is accurately transferred to the internal sensor.

Implementations of external diaphragms are incorporated into the enhanced pressure sensing system to address such issues. For instance, some implementations of the external diaphragm include a metallized layer or other highly impermeable layer to furnish a high degree of seal at least near to hermetic grade. Implementations can include various structural considerations of the external diaphragm that allow for a regulated adjustment of volume containing the internal intermediary fluid to allow for expansion and contraction of the intermediary fluid due to temperature change to diminish changes in pressure of the intermediary fluid due to such temperature change. As temperature of the intermediary fluid changes, the external diaphragm is able to move in a direction that minimizes differential pressure across the external diaphragm over an operational temperature range (such as 0 to 100 degrees Celsius or 33 to 43 degrees Celsius) thereby reducing pressure change of the intermediary fluid due to change in temperature of the intermediary fluid. Implementations can also include structural considerations of the external diaphragm, which would allow for a relatively smooth hydrodynamic surface to reduce possibilities of inducing shearing motion in sampled fluid flow.

Implementations of the external diaphragm include a bi-layer construction to provide hermetic-like sealing and an ability to expand and contract to compensate for temperature change of the intermediary fluid. The two layers of the bi-layer external diaphragm can have a similar thickness and can be made from materials of comparable elastic modulus but maximally different coefficients of thermal expansion (CTE). Alternately, if the elastic moduli are different, the thicknesses of the materials of the two layers of the bi-layer external diaphragm can be chosen so that the stiffness of each layer is approximately equal to increase deflection of the diaphragm with temperature. Examples are two metal layers (where the thicknesses would be comparable) or a ceramic coated with a polymer (where the polymer layer would be much thicker than the ceramic).

In some implementations, one of the layers, such as the layer contacting the intermediary fluid, can be made from an impermeable material that allows the housing of the pressure sensor system to be hermetic or near-hermetic. Implementations include one of the layers of the bi-layer external diaphragm (such as the external layer in contact with the sampled fluid) to have a hemocompatible outer surface material to reduce risk of thrombus formation.

In some implementations, the thickness of the first layer and the thickness of the second layer are sized according to in part the difference between the coefficient of thermal expansion of the intermediary fluid and the coefficient of thermal expansion of the housing portions defining a chamber containing the intermediary fluid and also according to in part the difference between the coefficient of thermal expansion of the first layer and second coefficient of thermal expansion of the second layer to allow for expansion of the chamber when temperature of the intermediary fluid and the housing portions is increased for conditions including over an operational temperature range of the pressure measuring system.

An exemplary version of the pressure sensing system is depicted herein as a representative example of how the bi-layer external diaphragm is used with a MEMS diaphragm positioned with a MEMS pressure sensor die in a housing to indirectly sample pressure state of a fluid being measured. The external diaphragm is used to make direct contact with the fluid being measured. Pressure state of the fluid being measured is transferred from the external diaphragm in direct contact through an electrically insulating intermediary fluid to the MEMS diaphragm thereby allowing the MEMS pressure sensor die to indirectly sample pressure state of the fluid being measured. Electrically conductive support members and electrically conductive solid vias are used to electrically couple circuitry outside the housing.

Figure 1:
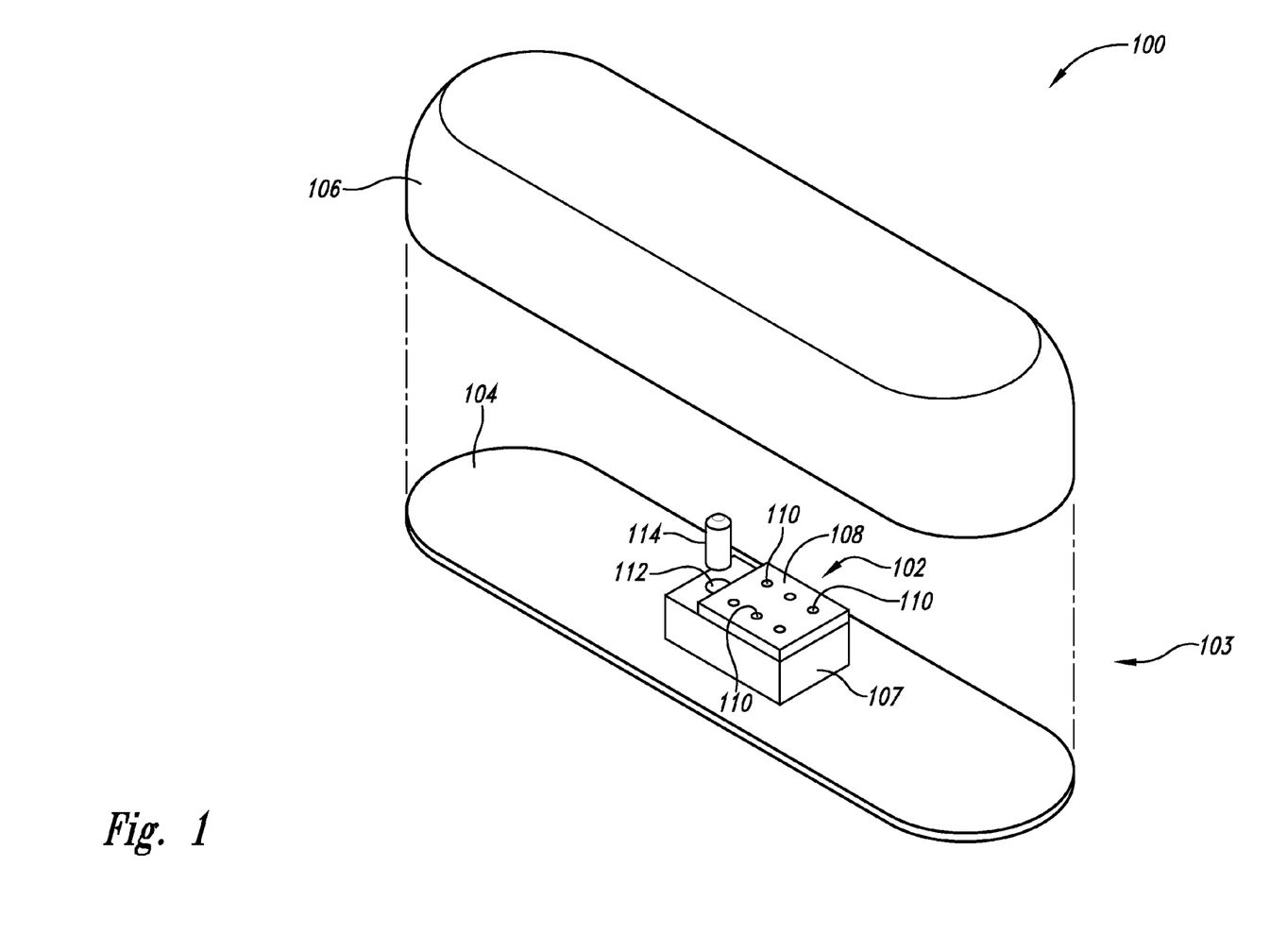
FIG. 1 is a perspective view of a pressure sensing system with the cover removed.

An exemplary pressure sensing system 100 is depicted in FIG. 1 as having a pressure sensing assembly 102 enclosed by a component package 103 having a package base 104 and a cover 106 shaped to sealably couple with the package base. In some implementations, the package base 104 can be made from a substrate material. The pressure sensing assembly 102 is integrally jointed with the package base 104 with a portion of the package base serving as a wall for the pressure sensing assembly 102.

Figure 4:
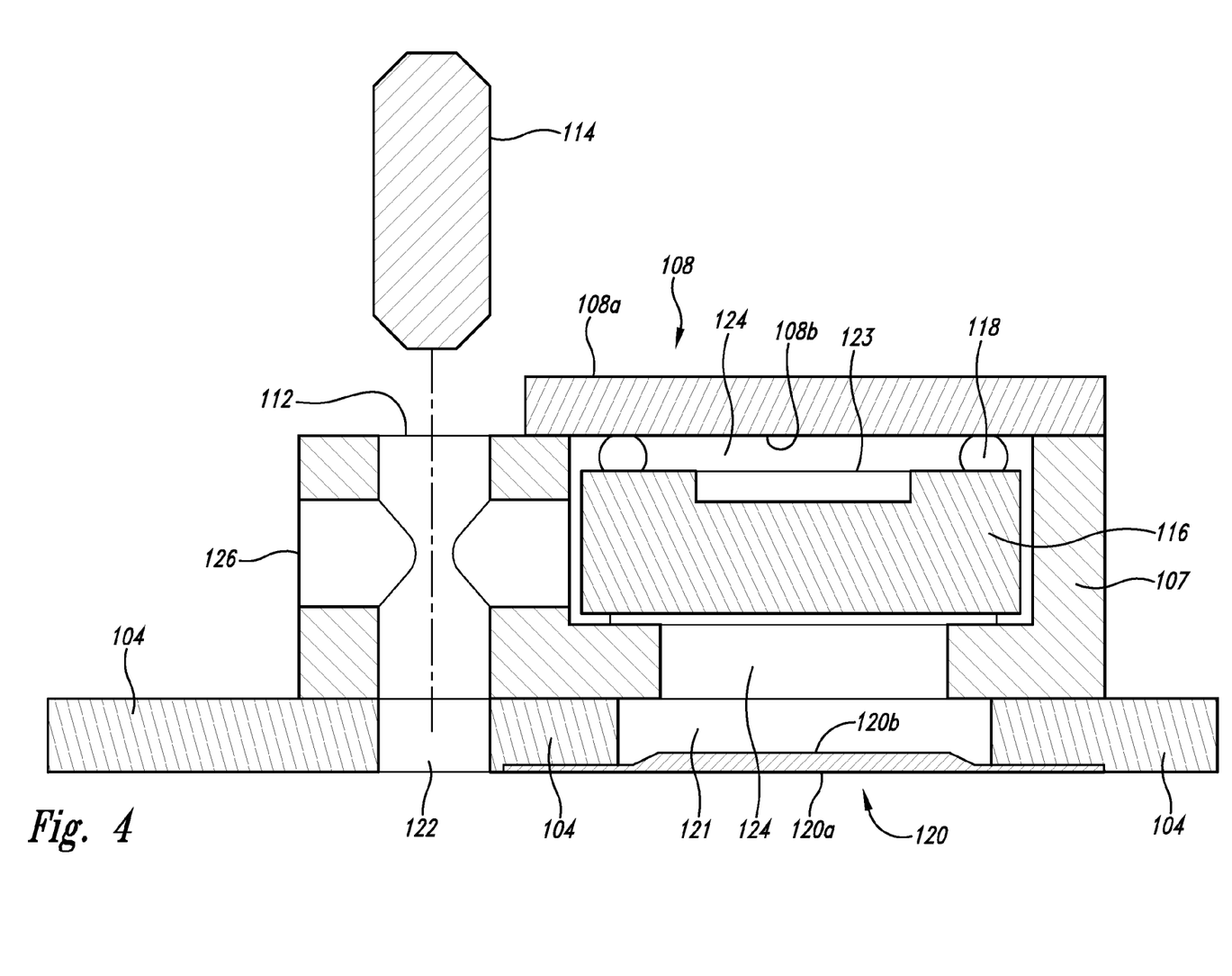
FIG. 4 is a sectional view of the pressure sensing system taken along the 4-4 line of FIG. 3.

The pressure sensing assembly 102 includes a housing 107 with a housing cover 108 having an exterior surface 108a, an interior surface 108b, and conductive solid vias 110 extending therebetween (better shown in FIG. 4). The housing 107 can be formed from ceramic and attached to the package base 104 with epoxy, silicone, brazing, or other attachment means. Alternatively, the housing 107 can be formed from metal and attached to the package base 104 with epoxy, silicone, brazing, laser welding, or other attachment means. As depicted, the housing cover 108 can be a hybrid printed circuit board formed from glass, ceramic, or other mechanically stable material compatible with technology involving printed circuitry. The housing cover 108 can be sealed to the housing 107 such as with epoxy, silicone, or braze. The housing 107 also includes a plughole 112 sized to receive a plug 114.

Figure 2:
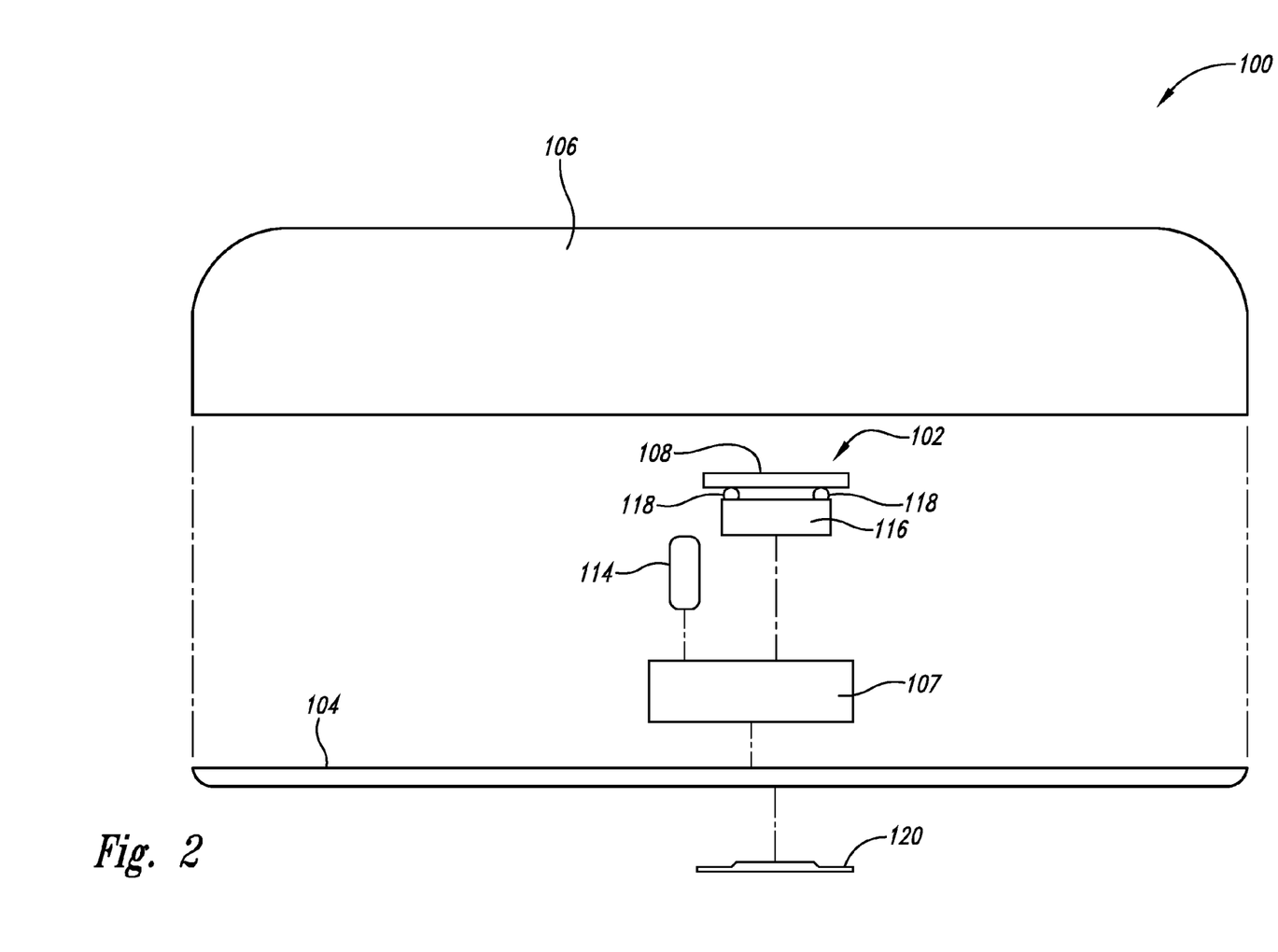
FIG. 2 is an exploded side elevational view of the pressure sensing system of FIG. 1.

As shown in FIG. 2, the pressure sensing assembly 102 further includes a MEMS pressure sensor die 116 that is in electrical contact with electrically conductive support members 118, which in turn are in electrical contact with the electrically conductive solid vias 110 further discussed below. The MEMS pressure sensor die 116 can be designed to determine fluid pressure levels either through capacitive or piezoresistive means. The conductive support members 118 also mechanically couple the MEMS pressure sensor die 116 to the housing cover 108. In some implementations, portions of solder, such as solder bumps, or other types of bumps such as stud bumps which are typically made of gold, are used for the conductive support members 118. Also shown in FIG. 2 as included with the pressure sensing assembly 102 is a external diaphragm 120 that is positioned to seal a housing aperture 121 shown in cross-section in FIG. 4, in that portion of the package base 104 that serves as a wall of the pressure sensing assembly. The external diaphragm 120 can be attached to the package base 104 by laser welding, epoxy, silicone, electrochemical bonding, electrochemical forming, brazing or other means. The external diaphragm 120 has a first layer 120a to contact a fluid being measured that has a pressure value that is desired to be known and an oppositely facing second layer 120b.

Figure 3:
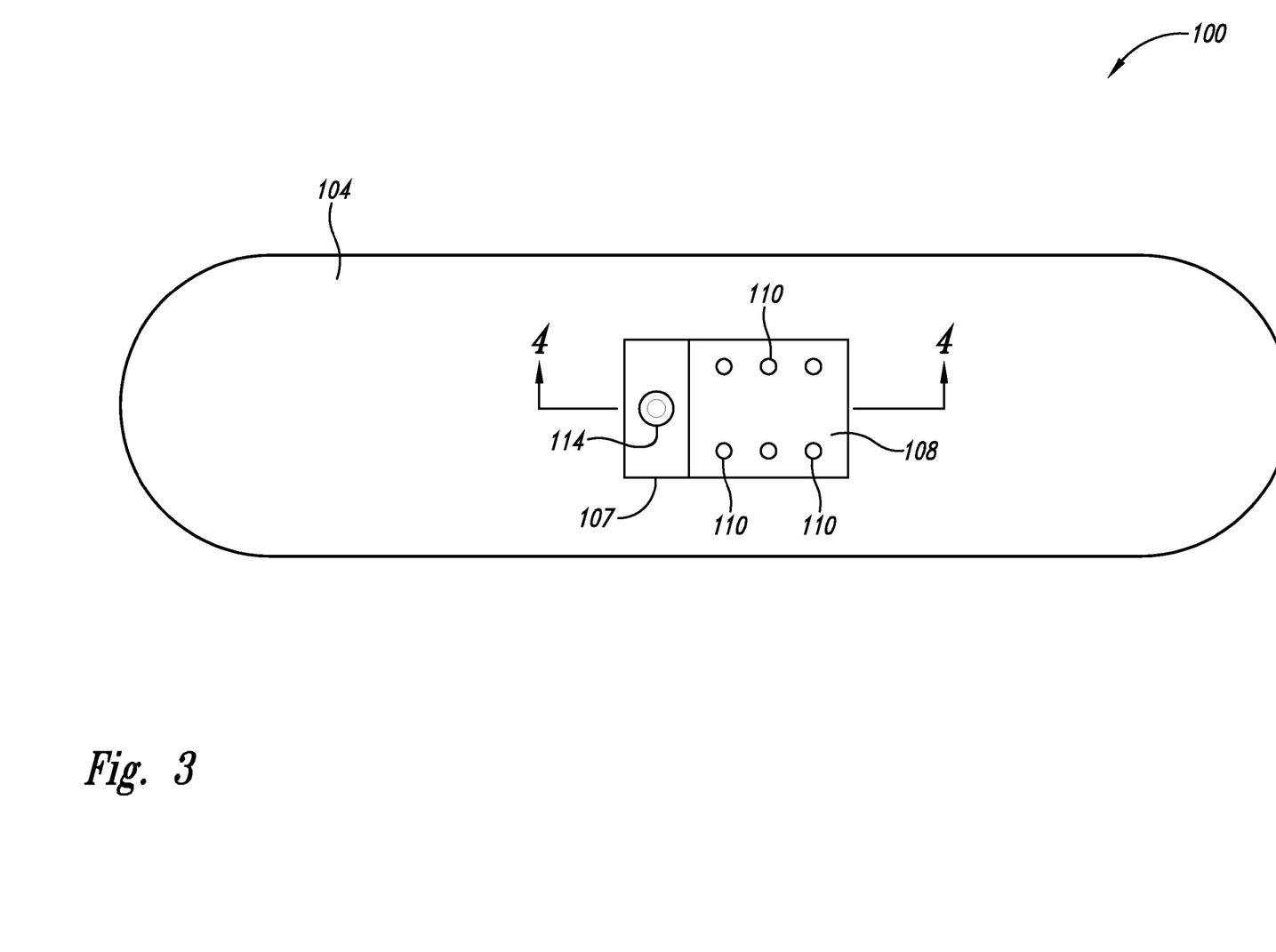
FIG. 3 is a top plan view of the pressure sensing system of FIG. 1 without the cover.

As indicated in FIG. 3, a sectional view of the pressure sensing assembly 102 is found in FIG. 4 showing the package base 104 to have a plug aperture 122 communicating with the plughole 112. As is shown, the MEMS pressure sensor die 116 has a MEMS diaphragm 123 in communication with a chamber 124 defined in part by the external diaphragm and housing portions including the package base 104, the housing 107, and the housing cover 108. The chamber 124 contains an intermediary fluid 125, which is used to transfer pressure applied to the first layer 120a of the external diaphragm 120 to the MEMS diaphragm 123. A fill port 126 is also in communication with the chamber 124 when the plug 114 is removed from the plughole 112 to fill the chamber with the intermediary fluid 125. The fill port 126 can be machined in the housing 107 and provides access to the chamber 124. The plughole 112 can be drilled in the housing 107 to receive the plug 114, which is used to seal the fill port 126 and the chamber 124 after the chamber has been filled with the intermediary fluid. The plug 114 can be made as a stopcock or other device to seal the fill port 126 and the chamber 124 as long as the volume of the sealed chamber has the same value each time the chamber is sealed.

Figure 5:
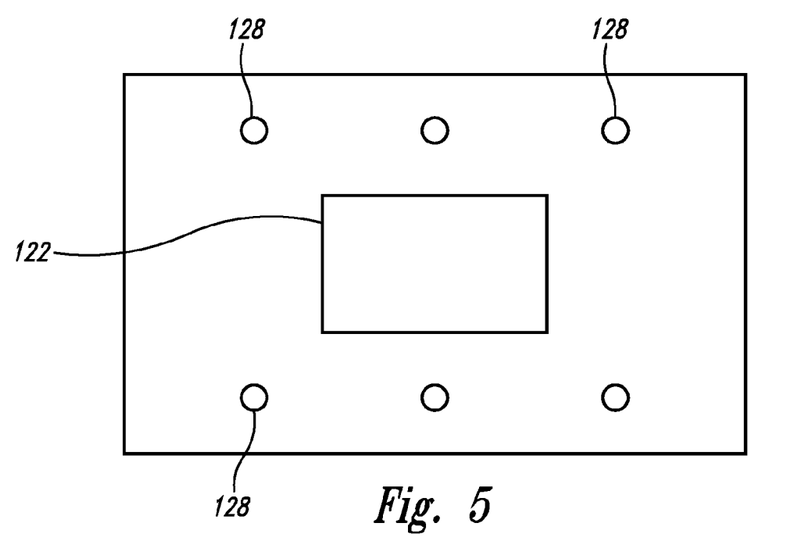
FIG. 5 is a top plan view of a MEMS pressure sensing die of the pressure sensing system of FIG. 1.
Figure 6:
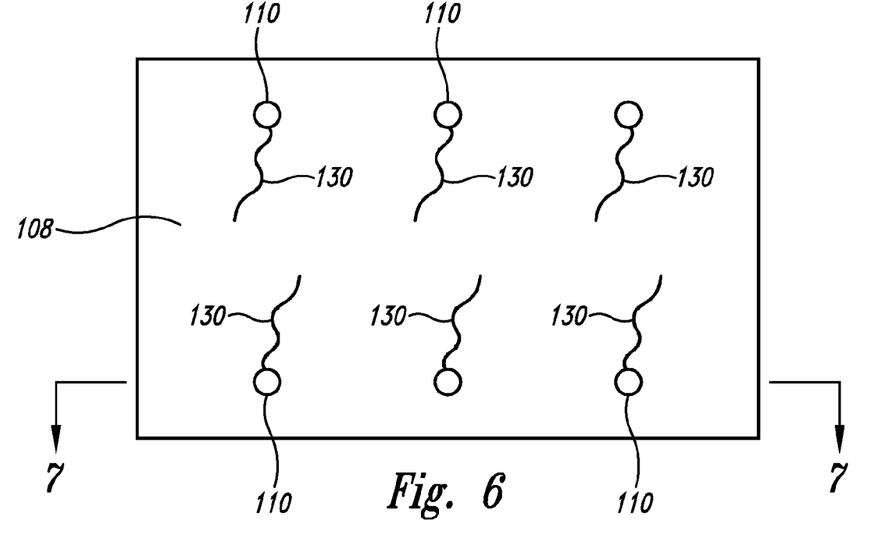
FIG. 6 is a top plan view of a sensor containment cover of the pressure sensing system of FIG. 1.
Figure 7:
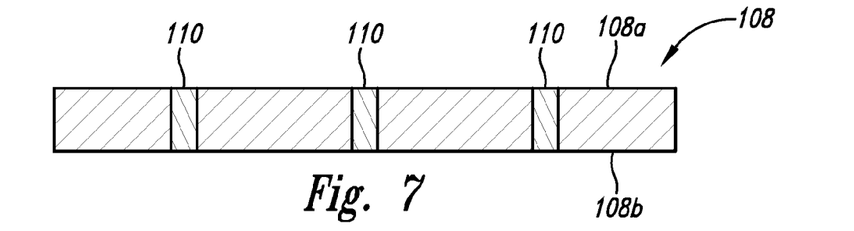
FIG. 7 is a sectional view of the sensor containment cover taken along the 7-7 line of FIG. 6.

The MEMS pressure sensor die 116 is shown in FIG. 5 to include electrical circuitry contacts 128 used for electrical communication with the MEMS pressure sensor die, such as to output pressure values or status information from the MEMS pressure sensor die or to input control signals to the MEMS pressure sensor die. The circuitry contacts 128 of the MEMS pressure sensor die 116 are aligned with or otherwise electrically connected to the conductive solid vias 110 in the housing cover 108, better shown in FIGS. 6 and 7 to conduct the electrical communication with the MEMS pressure sensor die outside of the housing 107. The conductive solid core vias 110 of the housing cover 108 act as sealed electrical feedthrough interconnects between the exterior surface 108a and the interior surface 108b, which is electrically coupled to the electrical circuitry contacts 128 of the MEMS pressure sensor die 116 through the conductive support members 118. External wires 130 are attached to the external surface 108a of the conductive vias 110 with solder, wire bond, conductive epoxy or other electrical bonding method.

In operation, the chamber 124 is filled with an intermediary fluid 125 that is electrically insulating, such as a silicone-based fluid such as silicone oil, perfluorocarbon liquid, or other insulator based fluid. The chamber 124 can be vacuum filled with fluid by first placing the entire pressure sensing assembly in a vacuum chamber and evacuating it, and while under vacuum, immersing the assembly 102 in the fluid. As air pressure is reintroduced into the vacuum chamber, it forces the fluid to fill any internal spaces within the pressure sensing assembly, leaving to voids. The plug 114 can then be inserted into the plughole 112 to seal off the chamber 124. Alternately, an additional plughole 112 and an additional fill port 126 can be used as a vent to introduce pressurized silicone oil or other pressurized fluid in the chamber 124. After filling the chamber 124, all of the plugholes 112 each would be sealed with one of the plugs 114.

External fluid pressure impinging upon the first layer 120a of the external diaphragm 120 sealing the housing aperture 121 of the package base 104 is transferred to the intermediary fluid 125 in the chamber 124 through the external diaphragm whereby the MEMS diaphragm is affected and the MEMS pressure sensor die senses a pressure level corresponding to the external fluid pressure.

Now turning to further discuss the external diaphragm 120 in more detail, the external diaphragm 120 is generally configured to be able to move freely over the operating pressure range and also over the operating temperature range so that it does not introduce a significant pressure differential, which would result in an error in the pressure reading. In addition, the external diaphragm 120 must be maintained in a linear, elastic region, as opposed to a plastic region, as it is deformed, so that its behavior does not change over temperature and pressure cycles, altering the calibration of the sensor system.

The intermediary fluid 125 poses a challenge in that it expands volumetrically with increasing temperature at a rate higher than the housing, resulting in an outward pressure on the external diaphragm 120. The amount of fluid expansion is characterized by the coefficient of thermal expansion (CTE) for the intermediary fluid 125.

Figure 8A:
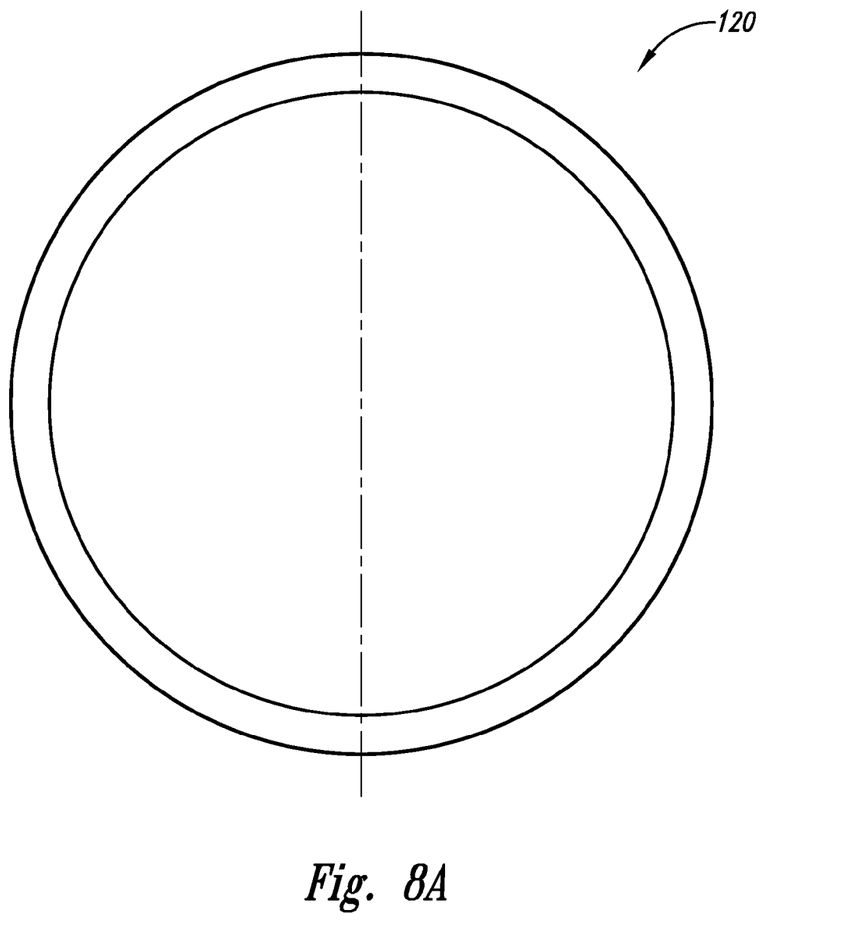
FIG. 8A is a top plan view of an enhanced external diaphragm of the pressure sensing system.
Figure 8B:
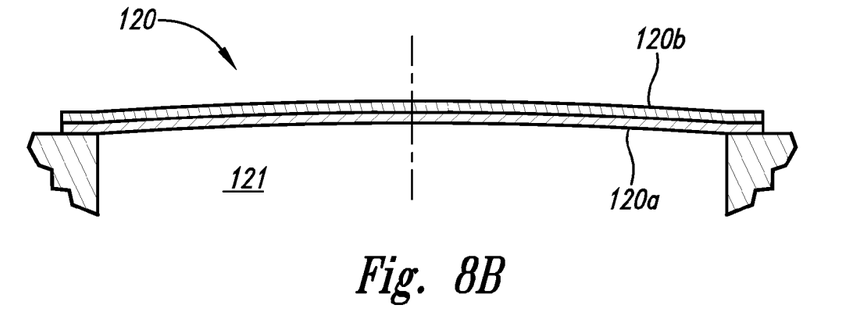
FIG. 8B is a sectional view of the external diaphragm of FIG. 8A.

A first implementation of the external diaphragm 120 is shown in FIG. 8A and FIG. 8B with the first layer 120a and the second layer 120b having different thickness and different thermal expansion coefficients. The first layer 120a is made from an impermeable material to allow the external diaphragm 120 to hermetically seal the intermediary fluid 125. For instance, the first layer 120a could be a sputtered, evaporated, or plated metal film on the second layer 120b, which could be a plastic material.

Being made of a plastic material, the second layer 120b would have a much higher CTE than the metal material of the first layer 120a so that the external diaphragm 120 would dome outward away from the chamber 124 and toward the sampled fluid as the temperature of the diaphragm and the intermediary fluid 125 increased. This thermal expansion would increase the volume of the chamber 124 and given appropriate sizing of the first layer 120a and the second layer 120b relative to the dimensions of the chamber, the volume of the chamber could expand at the same rate as the volumetric expansion of the intermediary fluid 125. In this implementation, the exterior surface of the second layer 120b in contact with the sampled fluid being measured is smooth to minimize thrombus formation.

Figure 9A:
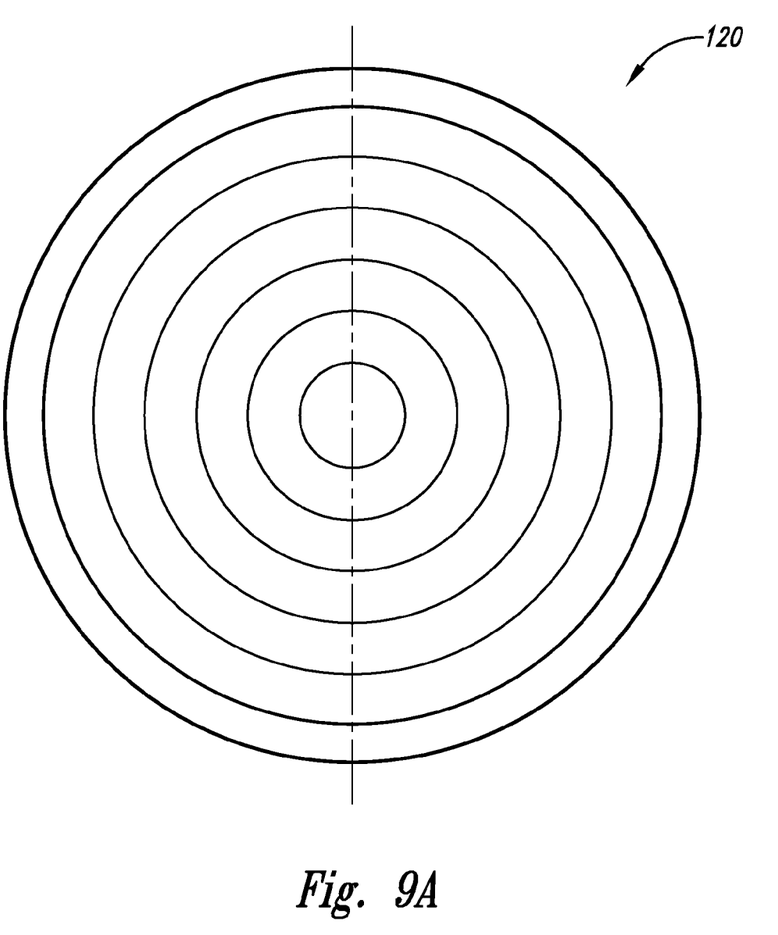
FIG. 9A is a top plan view of a corrugated version of the external diaphragm of FIG. 8A.
Figure 9B:
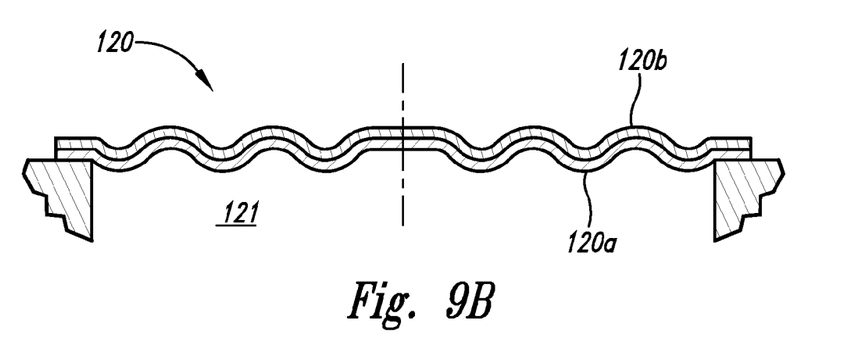
FIG. 9B is a sectional view of the corrugated external diaphragm of FIG. 9A.

A second implementation of the external diaphragm 120 is shown in FIG. 9A and FIG. 9B in which the first layer 120a and the second layer 120b are of a corrugated construction with the first layer and the second layer having different thickness and different thermal expansion coefficients. The corrugation of the first layer 120a and the second layer 120b increase the compliance of the external diaphragm 120, to reduce differential pressure across the external diaphragm as temperature of the intermediary fluid 125 changes. The first layer 120a is of an impermeable material to provide hermetic sealing of the intermediary fluid 125. The first layer 120a can be a sputtered, evaporated, or plated metal film on the second layer 120b, which can be of a plastic material.

The plastic material of the second layer 120b can have a much higher CTE than the metal material of the first layer 120a so that the external diaphragm 120 can dome outward as temperature of the intermediary fluid 125 is increased as further described above. Since the second implementation of the external diaphragm 120 has a corrugated exterior surface of the second layer 120b in contact with the sampled fluid, the second implementation does not minimize thrombus formation to the same extent as the first implementation of the external diaphragm with the smooth exterior surface of the second layer 120b.

Figure 10A:
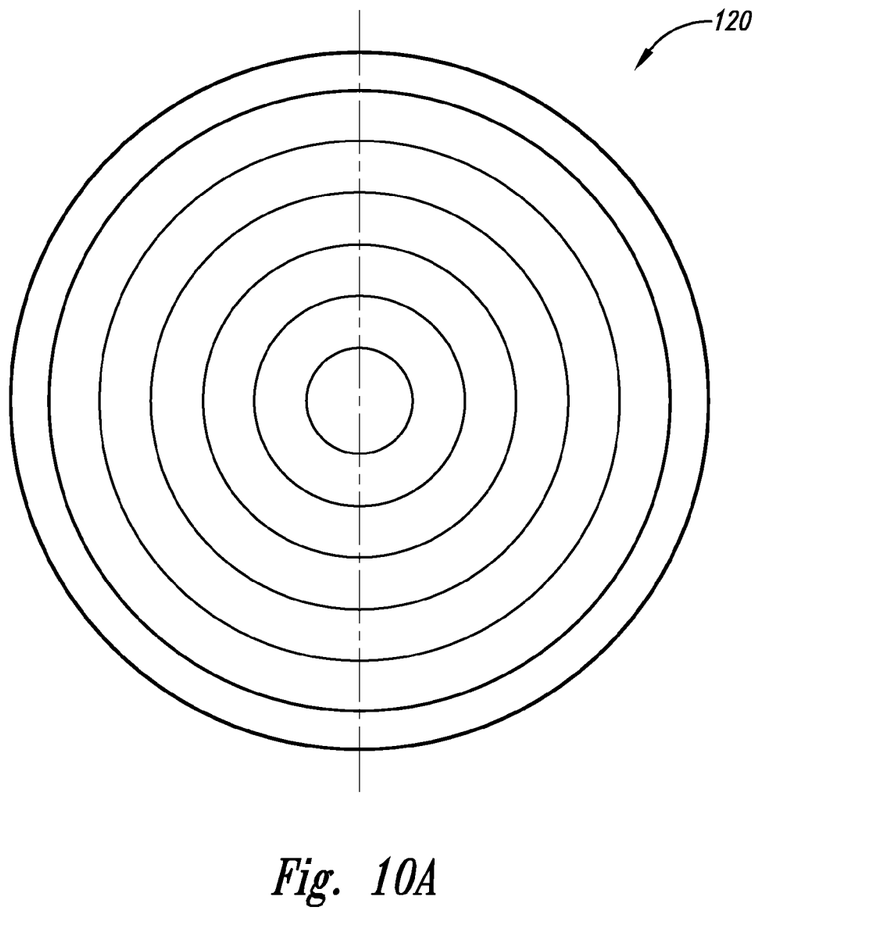
FIG. 10A is a top plan view of the corrugated external diaphragm of FIG. 9A with a filler material.
Figure 10B:
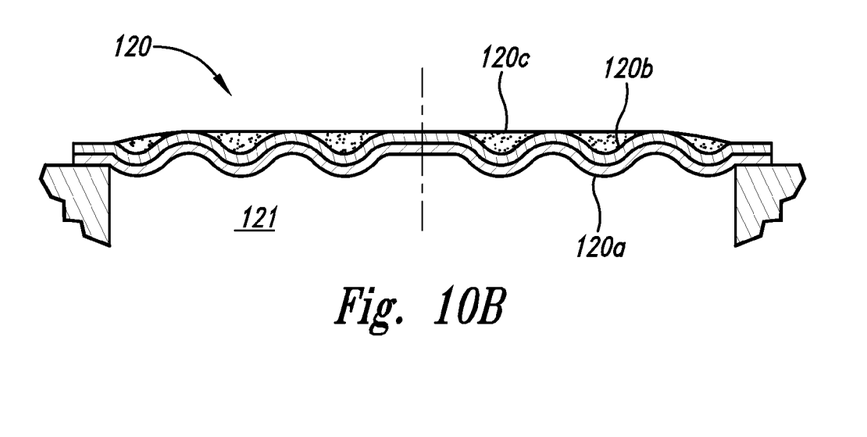
FIG. 10B is a sectional view of the corrugated external diaphragm with the filler material of FIG. 10A.

A third implementation of the external diaphragm 120 is shown in Figures FIG. 10A and FIG. 10B as having a corrugated first layer 120a and a corrugated second layer 120b having different thickness and different thermal expansion coefficients. The first layer 120a is impermeable to provide hermetic sealing for the intermediary fluid 125. The first layer 120a can be a sputtered, evaporated, or plated metal film on the second layer 120b, which could be a plastic material. The plastic material of the second layer 120b can have a much higher CTE than the metal material of the first layer 120a so that the external diaphragm 120 can dome outward as temperature of the intermediary fluid 125 as further described above.

As shown in FIG. 10B, the outer corrugated surface of the second layer 120b is filled with a hydrogel or a silicone, fluorosilicone, perfluorocarbon gel type first cover material 120c, which has a low modulus. The first cover material 120c provides a smooth outer surface of the external diaphragm that is in contact with the sampled fluid to minimize thrombus formation. The volumetric CTE of hydrogels and silicone, fluorosilicone, or perfluorocarbon gels for the first cover material 120c is typically 1065-1305 PPM/° C., and thus the linear CTE range is 355-435 PPM/° C. This is substantially higher than solid plastic materials used for the second layer 120b, which are in the range of 40-250 PPM/° C. (where the higher values correspond to soft materials such as silicone rubber). Thus, thermal expansion of the first cover material 120c can assist in causing the external diaphragm 120 to dome outward with increasing temperature of the intermediary fluid 125 (although this will be a weak effect, due to the low modulus of the gel).

Choosing a smooth outer surface material for the external diaphragm to contact the sampled fluid addresses the thrombus formation issue, but use of a silicone, fluorosilicone, or perfluorocarbon gel for the first cover material 120c is not ideal regarding hemocompatibility when the sampled fluid involves blood flow. Chemical mechanisms can also trigger a coagulation cascade, and use of silicone, fluorosilicone, or perfluorocarbon gel for the first cover material 120c can also elicit a foreign body response (leading to a series of events as host body seeks to encapsulate the cover material). Using a hydrogel for the first cover material 120c can minimize this problem, as certain hydrogel formulations are known to be well-tolerated in the bloodstream.

Figure 11A:
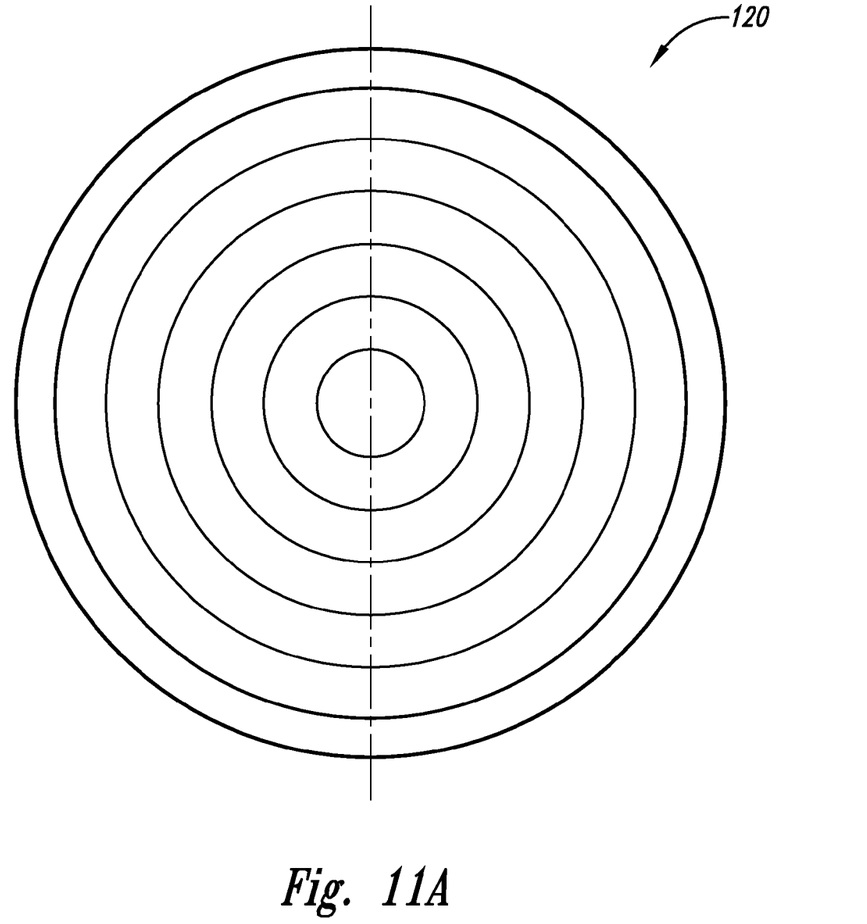
FIG. 11A is a top plan view of corrugated external diaphragm of FIG. 10A with an added external layer.
Figure 11B:
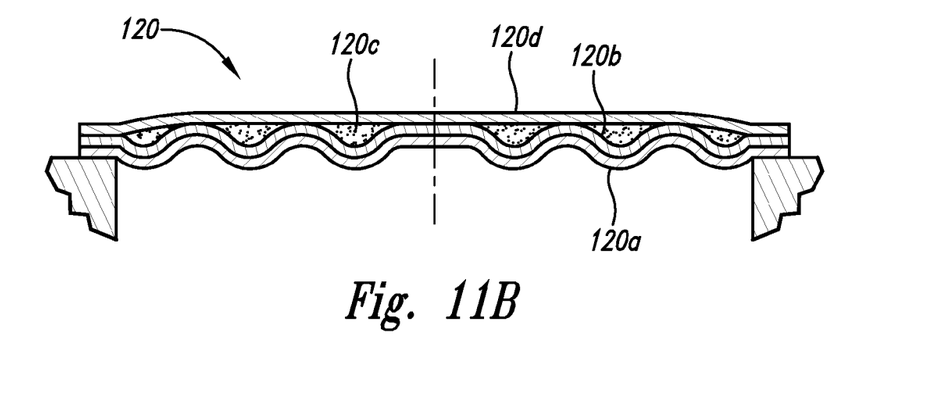
FIG. 11B is a sectional view of the corrugated external diaphragm with an added external layer of FIG. 11A.

A fourth implementation of the exterior diaphragm 120 is shown in FIG. 11A and FIG. 11B that incorporates aspects of the first layer 120a, the second layer 120b, and the first cover material 120c of the third implementation of the exterior diaphragm. Further included in the fourth implementation is a second cover material 120d, which covers the first cover material 120c. The second cover material 120d can provide a smooth surface and also have hemocompatibility properties, such as found with expanded polytetrafluoroethylene (ePTFE). The second cover material 120d of ePTFE can be made with a range of porosities, pore sizes, and surface characteristics, for instance, having similar characteristics as a vascular graft application, as both are in direct blood contact.

The ePTFE, being a porous Teflon material, has a very low tensile modulus of about 48.6 MPa, as compared to 552 MPa for solid PTFE and 3.45 GPa for polyetheretherketone (PEEK), a rigid plastic. Titanium, by comparison, is 110 GPa. Thus, the ePTFE layer will be highly compliant and will not interfere with normal pressure sensor operation. Choosing a smooth outer surface material for the second cover material 120d addresses the thrombus formation issue, and the ePTFE is a good choice from a hemocompatibility standpoint.

The pore size of ePTFE in a form that is used in vascular grafts is typically 10 to 30 microns, which is larger than blood cells (~8 microns) or other types of cells found in the blood. Using ePTFE with a smaller pore size (<8 microns) provides a surface that the cells cannot penetrate. Thus, cells cannot enter into the porous space within the material. Thus, the space, if the first cover material 120c is not used so that the space between the second layer 120b and the second cover material 120d is left unfilled at the time of implantation, the space becomes filled with fluid constituents of the blood. If the first cover material 120c is used to fill the space between the second layer 120b and the second cover material 120d, the first cover material could also be introduced into the porosity of the ePTFE of the second cover material, if so desired, to exclude fluid constituents of the blood from entering into the pore space of the second cover material. In this case, the ePTFE pore size could be larger than a blood cell, if so desired. Using a first cover material 120c that readily wets ePTFE and which has low solubility in the bloodstream, such as a perfluorocarbon-based gel or liquid, offers the added advantage that the material 120c will largely remain in place within the ePTFE. It is hypothesized that filling the ePTFE porosity with the first cover material may improve sensor longevity in the body, as it would prevent biofouling from occurring within the ePTFE over extended periods.

From the foregoing it will be appreciated that, although specific implementations have been described herein for purposes of illustration, various modifications may be made without deviating from the spirit and scope of the invention.

The invention claimed is:

1. For measuring pressure of a sampled fluid within a biological structure, an implantable system comprising
a plurality of housing portions having an overall coefficient of thermal expansion;
an intermediary fluid having a coefficient of thermal expansion greater than the overall coefficient of thermal expansion of the plurality of housing portions;
an external diaphragm including a first diaphragm portion having a first coefficient of thermal expansion, the first diaphragm portion positioned in the external diaphragm to contact the intermediary fluid when the external diaphragm is sealing the aperture with the pressure measuring system implanted in the biological structure, and a second diaphragm portion having a second coefficient of thermal expansion, the second diaphragm portion in juxtaposition with the first diaphragm portion;
a chamber defined by the housing portions and the external diaphragm; and
an aperture sealed by the external diaphragm to prevent passage of the intermediary fluid from the chamber through the aperture, apart from being sealed by the external diaphragm, the aperture otherwise in fluid communication with the chamber, the first diaphragm portion and the second diaphragm portion, shaped, sized, and positioned in the external diaphragm to cause the external diaphragm to expand away from the chamber to increase volume of the chamber when temperature of the intermediary fluid and the housing portions increases to substantially compensate for the difference between the coefficient of thermal expansion of the intermediary fluid and the overall coefficient of thermal expansion of the housing portions and geometrical configuration of the housing portions to allow the pressure level of the intermediary fluid to be substantially unaffected by changes in temperature of the intermediary fluid for conditions including over an operational range of the pressure measuring system.

2. The system of claim 1, wherein the first diaphragm portion and the second diaphragm portion are corrugated, further including a first cover material positioned to fill corrugated surfaces of the second diaphragm portion.

3. The system of claim 2, wherein the first cover material is one of the following: a hydrogel, a silicone gel, a fluorosilicone gel, and a perfluorocarbon gel.

4. The system of claim 2, further including a substantially smooth second cover material positioned adjacent to the first cover material.

5. The system of claim 4, wherein the second cover material is substantially expanded polytetrafluoroethylene.

6. The system of claim 5, wherein the porosity of the second cover material is filled with a gel or a liquid.

7. The system of claim 1, wherein the first coefficient of thermal expansion of the first diaphragm portion is greater than the second coefficient of thermal expansion of the second diaphragm portion.

8. The system of claim 1, wherein the second diaphragm portion is positioned in the external diaphragm to be in contact with the sampled fluid when the external diaphragm is positioned to seal the aperture.

9. The system of claim 8, wherein the second diaphragm portion has a substantially smooth surface to contact the sampled fluid.

10. The system of claim 1, wherein the second diaphragm portion has a thickness greater than the first diaphragm portion.

11. The system of claim 1, wherein the first diaphragm portion is substantially impermeable to the intermediary fluid is assist in preventing passage of the intermediary fluid from the chamber when the external diaphragm is positioned to seal the aperture.

12. The system of claim 1, wherein the first diaphragm portion is coupled to the second diaphragm portion by at least one of the following: sputtering, evaporation, and plating.

13. The system of claim 1, wherein the first diaphragm portion is coupled to the second diaphragm portion as a thin metal film.

14. The system of claim 1, wherein the second diaphragm portion is a plastic material.

15. For measuring pressure of a sampled fluid within a biological structure, an implantable system comprising
a plurality of housing portions having an overall coefficient of thermal expansion;
an intermediary fluid having a coefficient of thermal expansion greater than the overall coefficient of thermal expansion of the plurality of housing portions;
an external diaphragm including a first layer having a first coefficient of thermal expansion and a first thickness and a second layer having a second coefficient of thermal expansion and a second thickness;
a chamber defined by the housing portions and the external diaphragm; and
an aperture sealed by the external diaphragm to prevent passage of the intermediary fluid from the chamber through the aperture, apart from being sealed by the external diaphragm, the aperture otherwise in fluid communication with the chamber,
the first layer being substantially impermeable and positioned in the external diaphragm to be in contact with the intermediary fluid when the external diaphragm is positioned to seal the aperture and when the chamber contains the intermediary fluid, and
the second layer in juxtaposition with the first layer, the second coefficient of thermal expansion of the second layer being greater by a second difference than the first coefficient of thermal expansion of the first layer, the first thickness of the first layer and the second thickness of the second layer being sized according to in part the first difference between the coefficient of thermal expansion of the intermediary fluid and the coefficient of thermal expansion of the housing portions and the second difference between the first coefficient of thermal expansion of the first layer and the second coefficient of thermal expansion of the second layer to allow for expansion of the chamber when temperature of the intermediary fluid and the housing portions is increased for conditions including over an operational temperature range of the pressure measuring system.

16. The system of claim 15, wherein the first layer and the second layer are corrugated, further including a first cover material positioned to fill corrugated surfaces of the second layer.

17. The system of claim 16, wherein the first cover material is one of the following: a hydrogel, a silicone gel, a fluorosilicone gel, and a perfluorocarbon gel.

18. The system of claim 16, further including a substantially smooth second cover material positioned adjacent to the first cover material.

19. The system of claim 18, wherein the second cover material is substantially expanded polytetrafluoroethylene.

20. The system of claim 19, wherein the porosity of the second cover material is filled with a gel or a liquid.

21. The system of claim 20 wherein the second layer is corrugated to increase compliance of the external diaphragm to reduce potential of a pressure differential forming across the external diaphragm as a result of temperature change of the intermediary fluid.

22. The system of claim 15, wherein the second layer is positioned in the external diaphragm to be in contact with the sampled fluid when the external diaphragm is positioned to seal the aperture.

23. The system of claim 22, wherein the second layer has a substantially smooth surface to contact the sampled fluid.

24. The system of claim 15, wherein the second layer has a thickness greater than the first layer.

25. The system of claim 15, wherein the first layer is substantially impermeable to the intermediary fluid is assist in preventing passage of the intermediary fluid from the chamber when the external diaphragm is positioned to seal the aperture.

26. The system of claim 15, wherein the first layer is coupled to the second layer by at least one of the following: sputtering, evaporation, and plating.

27. The system of claim 15, wherein the first layer is coupled to the second layer as a thin metal film.

28. The system of claim 15, wherein the second diaphragm portion is a plastic material.

29. For measuring pressure of a sampled fluid within a biological structure a method comprising
providing a plurality of housing portions having an overall coefficient of thermal expansion;
providing an intermediary fluid having a coefficient of thermal expansion greater than the overall coefficient of thermal expansion of the plurality of housing portions;
providing an external diaphragm including a first diaphragm portion having a first coefficient of thermal expansion and a second diaphragm portion having a second coefficient of thermal expansion;
providing a chamber defined by the housing portions and the external diaphragm; and
sealing an aperture sealed by the external diaphragm to prevent passage of the intermediary fluid from the chamber through the aperture; and
shaping, sizing, and positioning the first diaphragm portion and the second diaphragm portion in the external diaphragm to cause the external diaphragm to expand away from the chamber to increase volume of the chamber when temperature of the intermediary fluid and the housing portions increases to substantially compensate for the difference between the coefficient of thermal expansion of the intermediary fluid and the overall coefficient of thermal expansion of the housing portions and geometrical configuration of the housing portions to allow the pressure level of the intermediary fluid to be substantially unaffected by changes in temperature of the intermediary fluid for conditions including over an operational range of the pressure measuring system.

30. The method of claim 29, wherein the first diaphragm portion and the second diaphragm portion are corrugated, further including positioning a first cover material to fill corrugated surfaces of the second diaphragm portion.

31. The method of claim 30, wherein the first cover material is one of the following: a hydrogel, a silicone gel, a fluorosilicone gel, and a perfluorocarbon gel.

32. The method of claim 30, further including providing a substantially smooth second cover material; and positioning the second cover material adjacent to the first cover material.

33. The method of claim 32, wherein the second cover material is substantially expanded polytetrafluoroethylene.

34. The method of claim 33, wherein the porosity of the second cover material is filled with a gel or a liquid.

35. The system of claim 15, wherein the second diaphragm portion is shaped as corrugated.

36. The system of claim 15, wherein the first coefficient of thermal expansion of the first diaphragm portion is lesser than the second coefficient of thermal expansion of the second diaphragm portion.

37. The method of claim 29, further including positioning the second diaphragm portion in the external diaphragm to be in contact with the sampled fluid when the external diaphragm is positioned to seal the aperture.

38. The method of claim 37, wherein the second diaphragm portion has a substantially smooth surface to contact the sampled fluid.

39. The method of claim 29, wherein the second diaphragm portion has a thickness greater than the first diaphragm portion.

40. The method of claim 29, wherein the first diaphragm portion is substantially impermeable to the intermediary fluid is assist in preventing passage of the intermediary fluid from the chamber when the external diaphragm is positioned to seal the aperture.

41. The method of claim 29, further including coupling the first diaphragm portion to the second diaphragm portion by at least one of the following: sputtering, evaporation, and plating.

42. The method of claim 29, further including coupling the first diaphragm portion to the second diaphragm portion as a thin metal film.

43. The method of claim 29, wherein the second diaphragm portion is a plastic material.

44. For measuring pressure of a sampled fluid within a biological structure, a method comprising
providing a plurality of housing portions having an overall coefficient of thermal expansion;
providing an intermediary fluid having a coefficient of thermal expansion greater by a first difference than the overall coefficient of thermal expansion of the plurality of housing portions;
providing an external diaphragm including a first layer having a first coefficient of thermal expansion and a first thickness, the first layer being substantially impermeable and including a second layer having a second coefficient of thermal expansion and a second thickness, the second coefficient of thermal expansion of the second layer being greater by a second difference than the first coefficient of thermal expansion of the first layer;
providing a chamber defined by the housing portions and the external diaphragm; and
providing an aperture in fluid communication with the chamber;
sealing the aperture by the external diaphragm to prevent passage of the intermediary fluid from the chamber through the aperture;
positioning the first layer in the external diaphragm to be in contact with the intermediary fluid when the external diaphragm is positioned to seal the aperture and when the chamber contains the intermediary fluid, and
positioning the second layer in juxtaposition with the first layer; and
sizing the first thickness of the first layer and the second thickness of the second layer according to in part the first difference between the coefficient of thermal expansion of the intermediary fluid and the coefficient of thermal expansion of the housing portions and the second difference between the first coefficient of thermal expansion of the first layer and the second coefficient of thermal expansion of the second layer to allow for expansion of the chamber when temperature of the intermediary fluid and the housing portions is increased for conditions including over an operational temperature range of the pressure measuring system.

45. The method of claim 44, wherein the first layer and the second layer are corrugated, further including providing a first cover material and positioning the first cover material to fill corrugated surfaces of the second layer.

46. The method of claim 45, wherein the first cover material is one of the following: a hydrogel, a silicone gel, a fluorosilicone gel, and a perfluorocarbon gel.

47. The method of claim 45, further including providing a substantially smooth second cover material and positioning the second cover material adjacent to the first cover material.

48. The method of claim 47, wherein the second cover material is substantially expanded polytetrafluoroethylene.

49. The method of claim 48, wherein the porosity of the second cover material is filled with a gel or a liquid.

50. The system of claim 15, wherein the second layer is shaped as corrugated.

51. The system of claim 15, wherein the first coefficient of thermal expansion of the first layer is lesser than the second coefficient of thermal expansion of the second layer.

52. The method of claim 44, further including positioning the second layer in the external diaphragm to be in contact with the sampled fluid when the external diaphragm is positioned to seal the aperture.

53. The method of claim 52, wherein the second layer has a substantially smooth surface to contact the sampled fluid.

54. The method of claim 44, wherein the second layer has a thickness greater than the first layer.

55. The method of claim 44, wherein the first layer is substantially impermeable to the intermediary fluid is assist in preventing passage of the intermediary fluid from the chamber when the external diaphragm is positioned to seal the aperture.

56. The method of claim 44, wherein the first layer is coupled to the second layer by at least one of the following: sputtering, evaporation, and plating.

57. The method of claim 44, wherein the first layer is coupled to the second layer as a thin metal film.

58. The method of claim 44, wherein the second diaphragm portion is a plastic material.

* * * * *